US006590119B2

(12) United States Patent
Ferro et al.

(10) Patent No.: US 6,590,119 B2
(45) Date of Patent: Jul. 8, 2003

(54) METHODS FOR THE SYNTHESIS OF DIOXOALKANOIC ACID COMPOUNDS

(75) Inventors: Michael P. Ferro, Bridgewater, NJ (US); Kathleen A. McCoy, Frenchtown, NJ (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 10/053,367

(22) Filed: Nov. 7, 2001

(65) Prior Publication Data

US 2002/0107408 A1 Aug. 8, 2002

Related U.S. Application Data

(62) Division of application No. 09/565,791, filed on May 5, 2000, now Pat. No. 6,355,812.

(60) Provisional application No. 60/138,881, filed on Jun. 11, 1999.

(51) Int. Cl.[7] ........................ C07C 67/30; C07C 67/313; C07C 69/618

(52) U.S. Cl. ............................ 560/51; 560/12; 560/17; 560/42; 560/45; 560/47; 560/53; 560/104; 560/14; 562/429; 562/459; 562/463

(58) Field of Search ............................ 560/14, 12, 17, 560/42, 45, 47, 51, 53, 104; 562/429, 459, 463

(56) References Cited

U.S. PATENT DOCUMENTS 3,427,305 A 2/1969 Chinn
4,694,018 A 9/1987 Chinn
5,032,590 A 7/1991 Hubsch et al.
5,219,856 A 6/1993 Olson

FOREIGN PATENT DOCUMENTS

JP 10-237076 A 9/1998

OTHER PUBLICATIONS

Khanna et al.; "1,2–Diarylpyrroles as Potent and Selective Inhibitors of Cyclooxygenase–2"; J. Med Chem. 1997, 40; pp. 1619–1633.

Kapoor et al.; "Steroid Intermedicates. Synthesis and Transformations of 7–Aryl–4,7–dioxoheptanoic Acids"; J.C.S. Perkin I, 1973; pp. 2420–2424.

Short et al.; "Synthesis and Interconversion of 6–Aroyl–4–oxohexanoic Acids and 5–Aryl–2–Furanpropionic Acids. Antiinflammatory Agents."; J. Chem., 1969, vol. 6; pp. 713–722.

Seebach et al.; "Herstellung von 1,3–Diketonen und von Nitro–diketonen durch(1:1)–Acylierungen von Lithiumenolaten mit Acylchloriden"; Helvetica Chimica Acta—vol. 64, Fasc. 3(1981)—Nr. 72; pp 716–735. (Note: English language abstract provided.).

*Primary Examiner*—Ba K. Trinh

(57) ABSTRACT

The invention relates to improved methods of producing aryl dioxoalkanoic acid compounds and derivatives useful as intermediates for diarylpyrrole therapeutic agents by the alcoholysis of benzoylcyclohexanone ketal compounds.

1 Claim, No Drawings

METHODS FOR THE SYNTHESIS OF DIOXOALKANOIC ACID COMPOUNDS

This application is a divisional of Ser. No. 09/565,791 filed on May 5, 2000, now U.S. Pat. No. 6,355,812, which claims the priority of the provisional application No. 60/138,881.

FIELD OF THE INVENTION

The present invention is directed to methods for the synthesis of dioxoalkanoic acid compounds and derivatives useful as intermediates for diarylpyrrole therapeutic agents. More particularly, the present invention is directed to the treatment of benzoylcyclohexanone compounds with an alcohol to provide improved yields of purified 7-aryl4,7-dioxoheptanoic acid derivatives.

BACKGROUND OF THE INVENTION

Aryl dioxoalkanoic acid compounds are useful intermediates for the synthesis of diarylpyrrole alkanoic acid therapeutic agents. U.S. Pat. No. 5,219,856 describes a process for preparing pyrrole compounds with activity as angiotensin-II inhibitors. U.S. Pat. No. 5,032,590 describes intermediate diphenyl isopropylpyrroles used to prepare substituted pyrrole compounds.

WO 9825896 and Collins, P. W., et al., 1,2-Diarylpyrroles as Potent and Selective Inhibitors of Cyclooxygenase-2, *J. Med Chem.,* 1997, 40, 1619–1633 disclose the preparation of 7-aryl-4,7-dioxoheptanoic acid compounds of the formula:

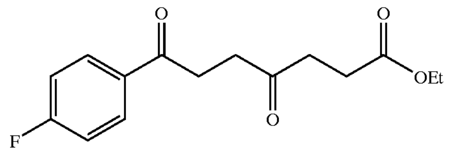

from acetophenones and furfural. These diketones have been used to prepare diarylpyrrole alkanoic acid therapeutic agents of the formula:

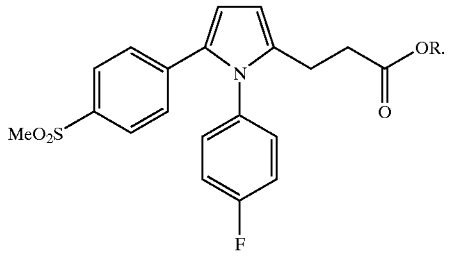

These references, however, teach the preparation of the diketone compounds using starting materials and processes that differ from that of the present invention and having yields of about 33%.

Diketone compounds have also been produced from aryloxo and aryldioxo pentanoic, hexanoic and heptanoic acid compounds. Kapoor, V. M., et al., Steroid Intermediates, Synthesis and Transformations of 7-Aryl4,7-dioxoheptanoic Acids, *J. Chem. Soc,* Perkin, 1973, 2420–2424. This reference discloses a process of preparing the aryldioxoheptanoic acid compounds using acid hydrolysis of furfurylidene compounds wherein the yields of the diketone compounds varied depending on the substituents used.

Similarly, aryl dioxoalkanoic acid compounds, such as aroyloxohexanoic acid, have been used as intermediates in the preparation of compounds with antiinflammatory activity. Short, F. W., et al., Synthesis and Interconversion of 6-Aroyl4-oxohexanoic Acids and 5-Aryl-2-furanpropionic Acids. Antiinflammatory Agents, *J. Heterocyclic Chem.,* 1969, 6, 713–722 describes the preparation of the aroyloxohexanoic acid compounds using acid catalyzed solvolysis. This reference teaches a process and starting materials that result in varying amounts of the desired diketone compounds.

The current methods used to prepare dioxoalkanoic acid compounds generally suffer from either the formation of the desired product in low yield, inseparable or hard to separate mixtures of the desired product and a different product or different products entirely. An object of the present invention is to provide a more efficient process to prepare purified diketone compounds with improved yields.

SUMMARY OF THE INVENTION

The present invention is directed to an efficient method for the synthesis of purified diketone compounds with improved yields. The process involves the treatment of benzoylcyclohexanone ketal compounds with an alcohol to unexpectedly produce mono-protected 1,4-diketone compounds such as 7-aryl-7,4-dioxoheptanones with surprisingly improved yields. More particularly, the invention provides a method of preparing a diketone compound of the general formula (I):

(I)

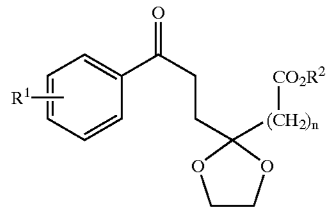

wherein:

$R^1$ is independently selected from the group consisting of hydrogen, halogen, —S—$CH_3$, —SO—$CH_3$, —$SO_2$—$CH_3$, —$SO_2$—$NH_2$,($C_1$–$C_6$)alkyl or substituted ($C_1$–$C_6$)alkyl;

wherein the alkyl substituents are selected from —S—$CH_3$, —SO—$CH_3$, —$SO_2$—$CH_3$ or —$SO_2$—$NH_2$, ($C_1$–$C_6$) alkoxy, cycloalkyl, aryl, aralkyl, nitro, amino, hydroxy or trifluoro;

$R^2$ is independently selected from the group consisting of ($C_1$–$C_6$)alkyl or substituted ($C_1$–$C_6$)alkyl; and, n is an integer selected from 1, 2 or 3; which method comprises, treatment of a compound of the general formula (II):

(II)

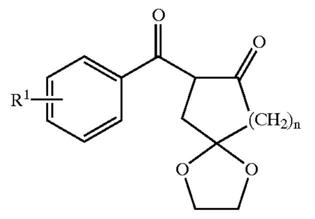

with an alcohol, wherein $R^1$ is as described above, to provide the diketone compounds of the general formula (I).

Preferably, the alcoholysis is carried out in refluxing alcohol. More preferably, the alcoholysis of the compound of the general formula (II) is carried out in the presence of a catalytic amount of sodium methoxide.

In an additional method of synthesis embodied in this invention, purified 7-aryl4,7-dioxoheptanoic acid compounds of the general formula (III) are produced with improved yields;

(III)

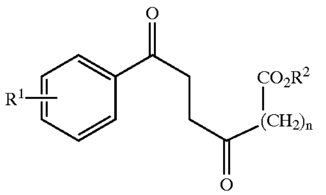

wherein $R^1$, $R^2$ and n are as recited above; which method comprises, transketalyzing or mildly hydrolyzing a diketone compound of the general formula (I) to prepare a 7-aryl4, 7-dioxoheptanoic acid compound of the general formula (III).

Aryl dioxoalkanoic acid compounds of the general formula (III) are demonstrated as useful intermediates in the preparation of diarylpyrrole therapeutic compounds of the general formula (IV), such as 1,5-diaryl-1H-pyrrole-2-propionic acids known to possess antiinflammatory activity;

(IV)

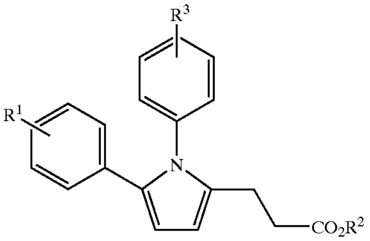

wherein;

wherein $R^1$ and $R^2$ are as recited above; and, $R^3$ is independently selected from the group consisting of hydrogen, halogen, —S—$CH_3$, —SO—$CH_3$, —$SO_2$—$CH_3$, —$SO_2$—$NH_2$, ($C_1$–$C_6$)alkyl or substituted ($C_1$–$C_6$)alkyl;

wherein the alkyl substituents are selected from —S—$CH_3$, —SO—$CH_3$, —$SO_2$—$CH_3$ or —$SO_2$—$NH_2$, ($C_1$–$C_{68}$) alkoxy, cycloalkyl, aryl, aralkyl; nitro, amino, hydroxy or trifluoro;

and the pharmaceutically acceptable salts thereof.

DETAILED DESCRIPTION OF THE INVENTION

Relative to the above generic description, certain compounds of the general formulae (I) and (III) are preferred. Particularly preferred embodiments are those compounds wherein;

$R^1$ is independently selected from the group consisting of hydrogen, halogen, —S—$CH_3$, —SO—$CH_3$, —$SO_2$—$CH_3$, —$SO_2$—$NH_2$ or ($C_1$–$C_4$)alkyl;

$R^2$ is independently selected from the group consisting of ($C_1$–$C_4$)alkyl or substituted ($C_1$–$C_4$)alkyl; and, n is an integer selected from 2 or 3;

and the pharmaceutically acceptable salts thereof.

Definitions

The terms used in describing the invention are commonly used and known to those skilled in the art. However, the terms that could have other meanings are hereinafter defined. These definitions apply to the terms as they are used throughout this specification, unless otherwise limited in specific instances, either individually or as part of a larger group.

Accordingly, the term "alkyl" refers to straight or branched chain unsubstituted hydrocarbon groups of 1 to 20 carbon atoms, preferably 1 to 6 carbon atoms. "Independently" means that when there are more than one substituent, the substituents may be different. The term "alkoxy" refers to O-alkyl where alkyl is as defined supra.

Unless otherwise specified, the term "substituted alkyl" refers to an alkyl group substituted by, for example, one to four substituents, such as, halo, trifluoromethyl, trifluoromethoxy, hydroxy, alkoxy, cycloalkyl, cycloalkyoxy, heterocylooxy, oxo, alkanoyl, aryloxy, alkanoyloxy, amino, alkylamino, arylamino, aralkylamino, cycloalkylamino, heterocycloamino, disubstituted amines in which the 2 amino substituents are selected from alkyl, aryl or aralkyl, alkanoylamine, aroylamino, aralkanoylamino, substituted alkanoylamino, substituted arylamino, substituted aralkanoylamino, thiol, alkylthio, arylthio, aralkylthio, cycloalkylthio, heterocyclothio, alkylthiono, arylthiono, aralkylthiono, alkylsulfonyl, arylsulfonyl, aralkylsulfonyl, sulfonamido (e.g. $SO_2NH_2$), substituted sulfonamido, nitro, cyano, carboxy, carbamyl (e.g. $CONH_2$), substituted carbamyl (e.g. CONH alkyl, CONH aryl, CONH aralkyl or cases where there are two substituents on the nitrogen selected from alkyl, aryl or aralkyl), alkoxycarbonyl, aryl, substituted aryl, guanidino and heterocyclos, such as indolyl, imidazolyl, furyl, thienyl, thiazolyl, pyrrolidyl, pyridyl, pyrimidyl and the like. Where noted above that the substituent is further substituted, such substitutions will be with halogen, alkyl, alkoxy, aryl or aralkyl.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl and diphenyl groups, each of which may be substituted.

The term "aralkyl" refers to an aryl group bonded directly through an alkyl group, such as benzyl.

The term "substituted aryl" refers to an aryl group substituted by, for example, one to four substituents such as alkyl, substituted alkyl, halo, trifluoromethoxy, trifluoromethyl, hydroxy, alkoxy, cycloalkyl, cycloalkyloxy, heterocyclooxy, alkanoyl, alkanoyloxy, amino, alkylamino, aralkylamino, cycloalkylamino, heterocycloamino, dialkylamino, alkanoylamino, thiol, alkylthio, cycloalkylthio, heterocyclothio, ureido, nitro, nitrile, cyano, carboxy, carboxyalkyl, carbamyl, alkoxycarbonyl, alkylthiono, arylthiono, alkysulfonyl, sulfonamido, aryloxy, alkoxycarbonyl, nitrile, furyl and the like. The substitutent may be further substituted by halo, hydroxy, alkyl, alkoxy, alkoxycarbonyl, nitrile, aryl, aryloxycarbonyl, substituted aryl, substituted alkyl, aralkyl, heterocyclyl and substituted heterocyclyl.

The term "cycloalkyl" refers to optionally substituted, saturated cyclic hydrocarbon ring systems, preferably containing 1 to 3 rings and 3 to 7 carbons per ring which may be further fused with an unsaturated $C_3$ to $C_7$ carbocyclic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above or one or more groups described above as alkyl substituents.

Exemplary substituents include one or more alkyl groups as described above or one or more groups described above as alkyl substituents.

The term “heteroatoms” shall include oxygen, sulfur and nitrogen.

Certain abbreviations used throughout this specification, particularly the Schemes and Examples, have the following meanings, unless specifically indicated otherwise:

| | |
|---|---|
| EtOH | Ethanol |
| h | hour |
| LiHMDS | Lithium hexamethyldisilazide |
| MeOH | Methanol |
| min | Minutes |
| NaOMe | Sodium methoxide |
| rt | Room temperature |
| THF | Tetrahydrofuran |

General Synthetic Methods

Representative compounds of the present invention are synthesized in accordance with the general method described below and illustrated in the schemes. Since the schemes are illustrations, the invention should not be construed as being limited by the chemical reactions and conditions expressed.

Various publications are cited throughout the description for this general scheme. The disclosure of these publications is hereby incorporated by reference into this application to describe more fully the state of the art to which this invention pertains.

Scheme 1 illustrates the preparation of benzoylcyclohexanone Compound 1b and subsequent methanolysis to the diarylpyrrole Compound 1e with improved yields. The cyclohexane-1,4-dione-monoethyleneglycol ketal Compound 1a is acylated under the conditions of Seebach, D., et al., *Helvetica Chimica Acta,* 1981, 64, 3, 716, which provides the diketone Compound 1b. The ring of the benzoylcyclohexanone Compound 1b may be opened to produce Compound 1c using refluxing methanol or, preferably, methanol at rt (room temperature) in the presence of a catalytic (cat) amount of sodium methoxide. The catalyzed reactions are complete in a few hours, while uncatalyzed reactions require several days. Double acid hydrolysis of the ketal-ester Compound 1c with equal portions of THF and 3N HCl over several hours at rt cleanly afford the diketo-acid Compound 1d. There was no evidence for the formation of yield-lowering furan side-products known in the art except after prolonged reaction times in acid. Heterocyclization of Compound 1d to the pyrrole Compound 1e was carried out in refluxing methanol, with or without a p-toluenesulfonic acid (ptsa) catalyst, and was complete in about 2 days. The catalyzed reactions yield methyl ester compounds; the reactions without ptsa form the acid compounds.

Scheme 1

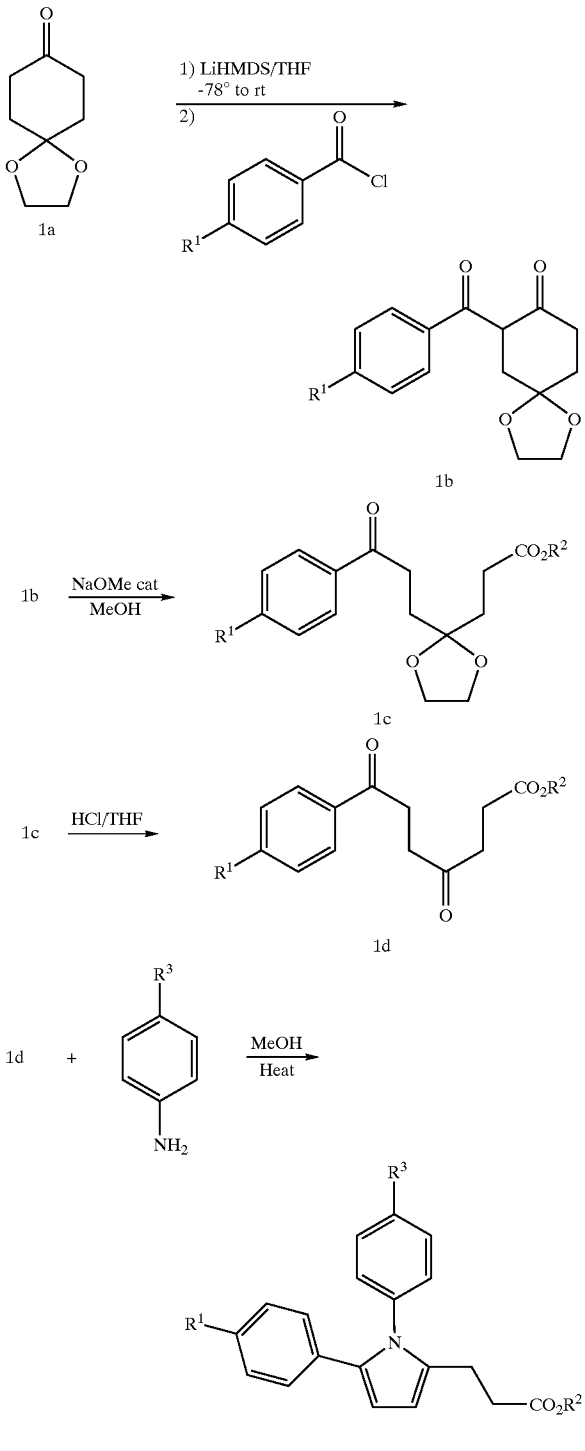

1a

1b

1c

1d

1e

Scheme 2 illustrates the preparation of sulfoxide Compound 2b from sulfide Compound 2a in low yield by oxidation with oxone. No sulfone was observed under these conditions. Sulfone Compound 2c was prepared using 4-methanesulfonylaniline in the cyclization (no ptsa). Compound 2c can be subsequently hydrolyzed to the acid Compound 2d. The cyclization reactions produce comparable yields for either the ester or acid compounds.

Scheme 2
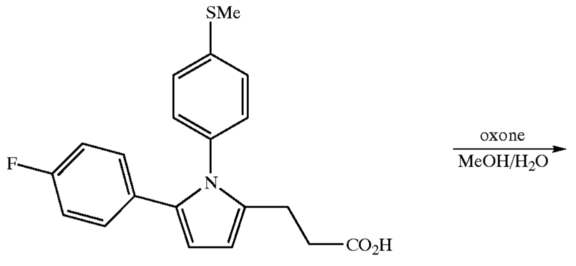
2a
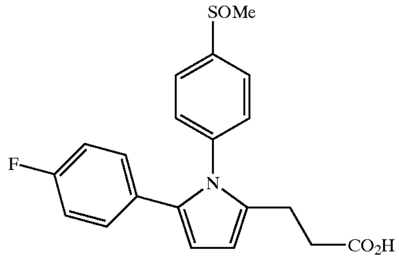
2b
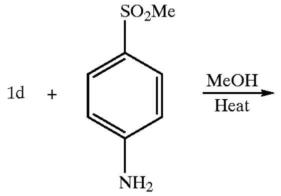
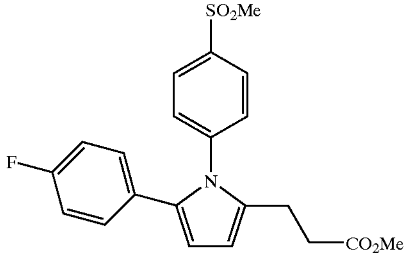
2c
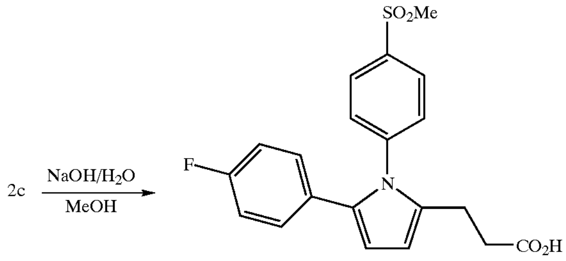
2d
Yields for the compound types prepared in Scheme 1 and Scheme 2 are compiled in Tables 1 to 4.
TABLE 1
Compound Yields
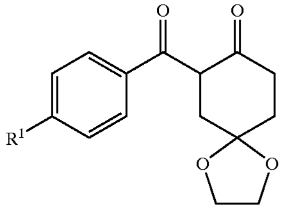
Compound 1b; Scheme 1
| $R^1$ | % Yield |
| --- | --- |
| Cl | 74 |
| F | 80 |
| $SO_2Me$ | 60 |
TABLE 2
Compound Yields
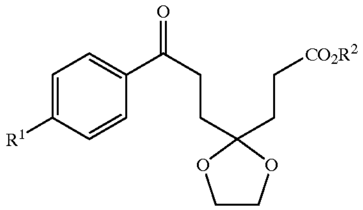
Compound 1c; Scheme 1
| $R^1$ | $R^2$ | % Yield |
| --- | --- | --- |
| Cl | Me | 96 |
| F | Me | 81 |
| $SO_2Me$ | Me | 24 |
TABLE 3
Compound Yields
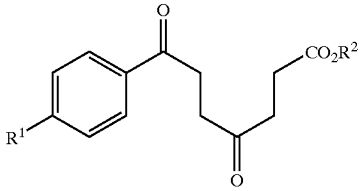
Compound 1d; Scheme 1
| $R^1$ | $R^2$ | % Yield |
| --- | --- | --- |
| Cl | H | 98 |
| F | H | 100 |
| $SO_2Me$ | H | 57 |

TABLE 4

Compound Yields

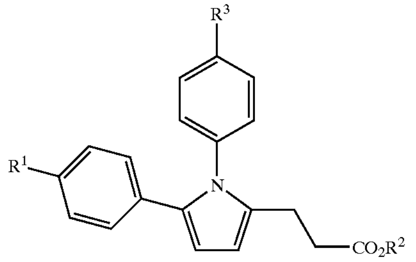

Compound 2a–2d; Scheme 2

Compound 1e; Scheme 1

| $R^1$ | $R^2$ | $R^3$ | % Yield |
|---|---|---|---|
| F | H | SMe | 67 |
| F | H | SOMe | 15 |
| F | Me | $SO_2Me$ | 80 |
| F | H | $SO_2Me$ | 89 |
| F | Me | SMe | 71 |
| $SO_2Me$ | H | F | 30 |
| Cl | Me | $SO_2NH_2$ | 96 |
| Cl | H | $SO_2NH_2$ | 88 |

The foregoing reactions are performed in a solvent appropriate to the reagents and materials employed and suitable for the transformation being effected. It is understood by those skilled in the art of organic synthesis that the various functionalities present on the molecule must be consistent with the chemical transformations proposed. This will frequently necessitate judgment as to the order of synthetic steps, protection of reactive groups, and selection of reaction conditions. Reaction conditions compatible with the substituents employed will be apparent to one skilled in the art, as will be the selection of protecting groups where needed.

From compounds of the general formula (II), it is evident that some of the compounds of the invention may have one or more asymmetrical carbon atoms in their structure. It is intended that the present invention include within its scope the stereochemically pure isomeric forms of the compounds as well as their racemates. Stereochemically pure isomeric forms may be obtained by the application of art known principles. Diastereoisomers may be separated by physical separation methods such as fractional crystallization and chromatographic techniques, and enantiomers may be separated from each other by the selective crystallization of the diastereomeric salts with optically active acids or bases or by chiral chromatography. Pure stereoisomers may also be prepared synthetically from appropriate stereochemically pure starting materials, or by using stereospecific reactions.

Suitable pharmaceutical salts are those of inorganic or organic acids, such as hydrochloric acid, hydrobromic acid, hydroiodic acid, sulfuric acid, nitric acid, phosphoric acid, acetic acid, succinic acid, oxalic acid, malic acid and the like. Suitable salts are also those of inorganic or organic bases, such as KOH, NaOH, $Ca(OH)_2$, $Al(OH)_3$, piperidine, morpholine, ethylamine, triethylamine and the like.

Also included within the scope of the invention are the hydrated forms of the compounds that contain various amounts of water, for instance, the hydrate, hemihydrate and sesquihydrate forms.

SPECIFIC SYNTHETIC EXAMPLES

The synthesis of specific, representative compounds of the present invention is presented in detail in the following example. This example is intended to illustrate a method of synthesis and is not intended to limit the scope of the claims in any way. Moreover, no attempt has been made to further optimize the yield obtained in this reaction. It would be obvious to one skilled in the art that variations in reaction time, temperature, solvents and/or reagents could increase the yields.

Example 1

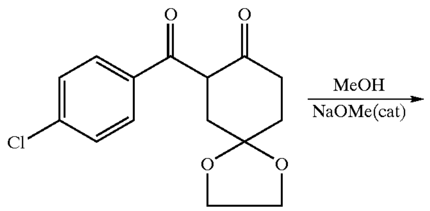

Compound 1a

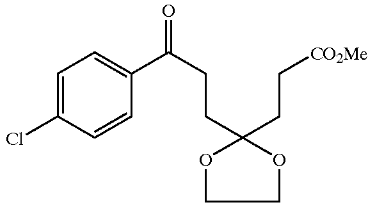

Compound 1b

The diketone Compound 1a (141 mg, 0.477 mMol) was dissolved in anhydrous methanol (2 mL) and treated with a NaOMe solution (25%, 0.20 mL) in anhydrous methanol at about rt. After about 1 h, the mixture was diluted with ethyl acetate (50 mL). The pH of the solution was carefully adjusted to about pH 2 with 2N HCl. Water (50 mL) was added and the ethyl acetate layer was dried with anhydrous sodium sulfate and filtered. Evaporation of the solvent afforded Compound 1b (150 mg, 96% yield) as a light tan solid.

We claim:

1. A method of producing 7-aryl4,7-dioxoheptanoic acid compounds of the general formula (III):

(III)

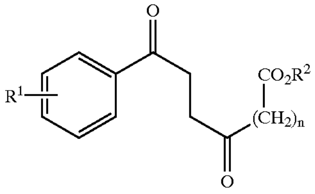

wherein $R^1$ is independently selected from the group consisting of hydrogen, halogen, —S—$CH_3$, —SO—$CH_3$, —$SO_2$—$CH_3$, —$SO_2$—$NH_2$, ($C_1$–$C_6$)alkyl or substituted ($C_1$–$C_6$)alkyl; wherein the alkyl substituents are selected from —S—$CH_3$, —SO—$CH_3$, —$SO_2$—$CH_3$ or —$SO_2$—$NH_2$, ($C_1$–$C_6$)alkoxy, cycloalkyl, aryl, aralkyl, nitro, amino, hydroxy or trifluoro;

$R^2$ is independently selected from the group consisting of ($C_1$–$C_6$)alkyl or substituted ($C_1$–$C_6$)alkyl; and, n is an integer selected from 1, 2 or 3; which method comprises, transketalyzing or mildly hydrolyzing a diketone compound of the general formula (I) to prepare a 7-aryl-4,7-dioxoheptanoic acid compound of the general formula (III).

* * * * *

UNITED STATES PATENT AND TRADEMARK OFFICE

CERTIFICATE OF CORRECTION

PATENT NO. : 6,590,119 B2
DATED : July 8, 2003
INVENTOR(S) : Ferro et al.

It is certified that error appears in the above-identified patent and that said Letters Patent is hereby corrected as shown below:

<u>Column 10,</u>
Line 39, "7-aryl4,7-dioxoheptanoic" should read -- 7-aryl-4,7-dioxoheptanoic --

Signed and Sealed this

Twenty-third Day of September, 2003

JAMES E. ROGAN
*Director of the United States Patent and Trademark Office*